United States Patent
Jabri et al.

(10) Patent No.: US 7,613,478 B2
(45) Date of Patent: Nov. 3, 2009

(54) METHOD AND SYSTEM FOR PORTABILITY OF CLINICAL IMAGES USING A HIGH-QUALITY DISPLAY AND PORTABLE DEVICE

(75) Inventors: Kadri N. Jabri, Waukesha, WI (US); Gopal B. Avinash, New Berlin, WI (US); Steve Fors, Chicago, IL (US)

(73) Assignee: General Electric Company, Schenectady, NY (US)

( * ) Notice: Subject to any disclaimer, the term of this patent is extended or adjusted under 35 U.S.C. 154(b) by 730 days.

(21) Appl. No.: 10/991,570

(22) Filed: Nov. 18, 2004

(65) Prior Publication Data

US 2005/0202844 A1 Sep. 15, 2005

Related U.S. Application Data

(63) Continuation-in-part of application No. 10/801,881, filed on Mar. 15, 2004, now Pat. No. 7,289,825.

(51) Int. Cl.
*H04M 1/00* (2006.01)
*H04N 7/114* (2006.01)
*G09G 5/08* (2006.01)

(52) U.S. Cl. ............... 455/556.1; 250/363.1; 715/840; 348/14.12; 600/1; 600/300; 600/437

(58) Field of Classification Search ............. 455/556.1; 348/14.12; 715/840; 600/1, 300, 437; 250/363.1
See application file for complete search history.

(56) References Cited

U.S. PATENT DOCUMENTS

| | | | |
|---|---|---|---|
| 6,325,756 B1 * | 12/2001 | Webb et al. ................. 600/300 |
| 6,468,265 B1 * | 10/2002 | Evans et al. ..................... 606/1 |
| 6,475,146 B1 * | 11/2002 | Frelburger et al. .......... 600/437 |
| 6,493,008 B1 * | 12/2002 | Yui ............................. 715/840 |
| 6,538,686 B2 * | 3/2003 | Hara et al. ................ 348/14.12 |
| 7,339,174 B1 * | 3/2008 | Hugg et al. .............. 250/363.1 |
| 7,375,338 B1 * | 5/2008 | Hugg et al. .............. 250/363.1 |
| 7,439,514 B1 * | 10/2008 | Uribe et al. .............. 250/363.1 |
| 7,470,907 B2 * | 12/2008 | Hugg et al. .............. 250/363.1 |
| 2005/0202844 A1 * | 9/2005 | Jabri et al. ................ 455/556.1 |
| 2008/0237472 A1 * | 10/2008 | Uribe et al. .............. 250/363.1 |
| 2008/0237473 A1 * | 10/2008 | Uribe et al. .............. 250/363.1 |
| 2008/0237476 A1 * | 10/2008 | Uribe et al. ............ 250/363.04 |
| 2008/0304619 A1 * | 12/2008 | Blevis et al. ................... 378/16 |

* cited by examiner

*Primary Examiner*—William D Cumming
(74) *Attorney, Agent, or Firm*—Hanley, Flight & Zimmerman, LLC

(57) ABSTRACT

Certain embodiments of the present invention provide a method and system for improved clinical workflow using wireless communication. A system for remote image display includes a data source with image data, wherein the data source is capable of transmitting the image data. The system also includes an identifiable display device capable of displaying image data transferred from the data source and a portable device capable of identifying the display device and requesting image data transfer from the data source to the display device without the transfer of the image data between the portable device and the data source. The system may also include an access point for relaying communication between the portable device and the data source. Communication between the portable device, the data source, and/or the display may include wireless communication, for example.

16 Claims, 7 Drawing Sheets

500

600

METHOD AND SYSTEM FOR PORTABILITY OF CLINICAL IMAGES USING A HIGH-QUALITY DISPLAY AND PORTABLE DEVICE

RELATED APPLICATIONS

The present application is a continuation-in-part of and claims priority from, U.S. patent application Ser. No. 10/801,881, filed on Mar. 15, 2004, now U.S. Pat. No. 7,289,825 and entitled "Method and System for Utilizing Wireless Voice Technology Within a Radiology Workflow".

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to wireless speech or other remote communication in a clinical environment. In particular, the present invention relates to use of wireless voice or other remote technology to improve clinical workflow.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

In a healthcare or clinical environment, such as a hospital, a large number of employees and patients may result in confusion or delay when trying to reach other medical personnel for examination, treatment, consultation, or referral, for example. A delay in contacting other medical personnel may result in further injury or death to a patient. Additionally, a variety of distraction in a clinical environment may frequently interrupt medical personnel or interfere with their job performance. Furthermore, workspaces, such as a radiology workspace, may become cluttered with a variety of monitors, data input devices, data storage devices, and communication device, for example. Cluttered workspaces may result in inefficient workflow and service to clients, which may impact a patient's health and safety or result in liability for a healthcare facility.

Data entry and access is also complicated in a typical healthcare facility. Speech transcription or dictation is typically accomplished by typing on a keyboard, dialing a transcription service, using a microphone, using a Dictaphone, or using digital speech recognition software at a personal computer. Such dictation methods involve a healthcare practitioner sitting in front of a computer or using a telephone, which may be impractical during operational situations. Similarly, for access to electronic mail or voice messages, a practitioner must typically use a computer or telephone in the facility. Access outside of the facility or away from a computer or telephone is limited.

Thus, management of multiple and disparate devices, positioned within an already crowded environment, that are used to perform daily tasks is difficult for medical or healthcare personnel. Additionally, a lack of interoperability between the devices increases delay and inconvenience associated with the use of multiple devices in a healthcare workflow. The use of multiple devices may also involve managing multiple logons within the same environment. A system and method for improving ease of use and interoperability between multiple devices in a healthcare environment would be highly desirable.

In a healthcare environment involving extensive interaction with a plurality of devices, such as keyboards, computer mousing devices, imaging probes, and surgical equipment, repetitive motion disorders often occur. A system and method that eliminates some of the repetitive motion in order to minimize repetitive motion injuries would be highly desirable.

Additionally, in a healthcare workflow, healthcare providers often consult or otherwise interact with each other. Such interaction typically involves paging or telephoning another practitioner. Thus, interaction between healthcare practitioners may be time- and energy-consuming. Therefore, there is a need for a system and method to simplify and improve communication and interaction between healthcare practitioners.

Healthcare environments, such as hospitals or clinics, include clinical information systems, such as hospital information systems (HIS) and radiology information systems (RIS), and storage systems, such as picture archiving and communication systems (PACS). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

In current information systems, such as PACS, information is entered or retrieved using a local computer terminal with a keyboard and/or mouse. During a medical procedure or at other times in a medical workflow, physical use of a keyboard, mouse or similar device may be impractical (e.g., in a different room) and/or unsanitary (i.e., a violation of the integrity of an individual's sterile field). Re-sterilizing after using a local computer terminal is often impractical for medical personnel in an operating room, for example, and may discourage medical personnel from accessing medical information systems. Thus, a system and method providing access to a medical information system without physical contact would be highly desirable to improve workflow and maintain a sterile field.

Imaging systems are complicated to configure and to operate. Often, healthcare personnel may be trying to obtain an image of a patient, reference or update patient records or diagnosis, and ordering additional tests or consultation. Thus, there is a need for a system and method that facilitate operation and interoperability of an imaging system and related devices by an operator.

In many situations, an operator of an imaging system may experience difficulty when scanning a patient or other object using an imaging system console. For example, using an imaging system, such as an ultrasound imaging system, for upper and lower extremity exams, compression exams, carotid exams, neo-natal head exams, and portable exams may be difficult with a typical system control console. An operator may not be able to physically reach both the console and a location to be scanned. Additionally, an operator may not be able to adjust a patient being scanned and operate the system at the console simultaneously. An operator may be unable to reach a telephone or a computer terminal to access information or order tests or consultation. Providing an additional operator or assistant to assist with examination may increase cost of the examination and may produce errors or unusable data due to miscommunication between the operator and the assistant. Thus, a method and system that facilitates operation of an imaging system and related services by an individual operator would be highly desirable.

Additionally, use of portable devices in a clinical environment is currently limited. Display quality on current portable devices is poor and insufficient for detailed medical viewing. For example, medical images displayed on portable devices may at best be used for illustration purposes, but the display quality is not adequate for diagnostic purposes. For images such as radiography images (e.g., computed radiography (CR), digital radiography (DR), and/or digitized film), for example, a diagnostic quality (e.g., high resolution and high dynamic range) display would be highly desirable.

Existing solutions involve plugging in a personal digital assistant (PDA) to a monitor and accessing data via an internet or intranet. In such a case, the PDA must store the images. However, PDAs have limited memory for large CR/DR full-resolution files. Additionally, images must be pre-loaded. A user is not able to dynamically pull up or query cases for review. Users are typically limited to a small set of images used for teaching purposes. Therefore, an improved system and method for displaying diagnostic quality images while bypassing PDA storage restrictions would be highly desirable.

Thus, there is a need for a system and method to improve clinical workflow using wireless communication or other remote technology.

BRIEF SUMMARY OF THE INVENTION

Certain embodiments of the present invention provide a method and system for improved clinical workflow using wireless communication. In an embodiment, a system for remote image display includes a data source including image data, wherein the data source is capable of transmitting the image data. The system also includes an identifiable display device capable of displaying image data transferred from the data source. The system further includes a portable device capable of identifying the display device and requesting image data transfer from the data source to the display device without the transfer of the image data between the portable device and the data source. In an embodiment, the system also includes an access point for relaying communication between the portable device and the data source.

In an embodiment, the display device may be a diagnostic quality display, for example. The data source may also include non-image data, for example. The display device may be capable of displaying the non-image data. In an embodiment, the portable device is a portable handheld device. Communication between the portable device, the data source, and/or the display device may include wireless communication, for example. Identification between the portable device and the display device may occur through wireless communication, for example.

Certain embodiments of a method for remote display of images in a healthcare environment include identifying a display device, requesting a transfer of image data from a data source to the display device, and displaying the data at the display device. The requesting step may include requesting the transfer of image data using a portable device. The transfer of the image data may occur without transfer of the image data between the portable device and the data source. The requesting step may also include requesting transfer of image data from the data source via a wireless connection. In an embodiment, the display device is a diagnostic quality display.

The method may also include relaying the request for data via an access point to the data source. In addition, the method may include controlling the display device. Furthermore, the method may include identifying the display device through wireless communication.

Certain embodiments of a wireless communication system for facilitating clinical workflow include a remote system in a healthcare environment, wherein the remote system is capable of being used for executing an operation, storing data, displaying data, and/or retrieving data, for example. The system also includes a wireless communication device for control of the remote system in the healthcare environment, wherein the wireless communication device allows centralized control of the remote system to facilitate executing an operation, storing data, displaying data, and/or retrieving data, for example. The system further includes an interface for relaying communication between the remote system and the wireless communication device, wherein the interface displays data from the remote system.

In an embodiment, the interface is integrated with the wireless communication device. The wireless communication device and the interface may control the remote system to perform data acquisition, data retrieval, order entry, dictation, audio playback, voice of IP conferencing, paging, data analysis, and/or display, for example. The interface may display data from the wireless communication device. In an embodiment, the wireless communication device is a wireless headset. In an embodiment, the interface is a portable handheld device. In an embodiment, the interface is a gaze tracking device.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

The present invention relates to a wireless voice communication system and method for improving workflow in a medical environment, such as radiology workflow, examination workflow, administrative workflow, physician workflow, or other clinical workflow. For purposes of illustration, certain embodiments will be described below in relation to a radiology workflow.

Figure 1:
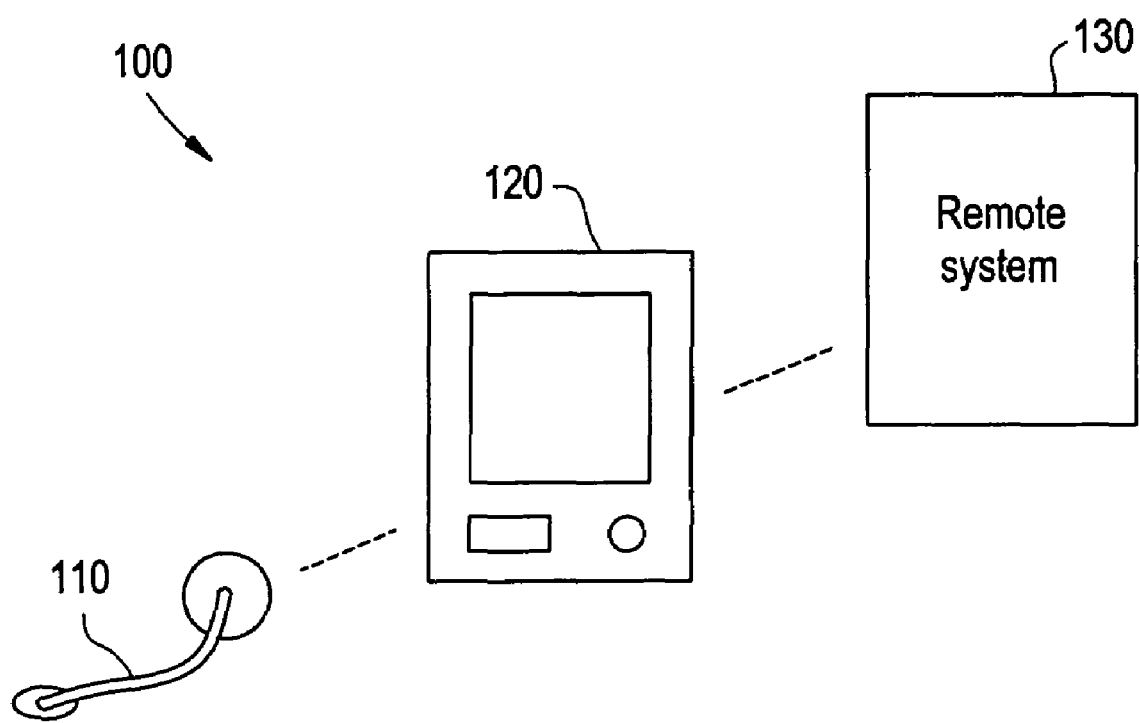
FIG. 1 illustrates a wireless voice communication system used in accordance with an embodiment of the present invention.

FIG. 1 illustrates a wireless voice communication system 100 used in accordance with an embodiment of the present invention. The system 100 includes a wireless communication device 110 and an interface 120. The communication device 110 and interface 120 allow a user to input and retrieve information from a remote system 130 and to execute functions at the remote system 130. The remote system 130 may be a personal computer, a workstation, a server, a picture archiving and communication system, an ECG system, a patient monitoring system, an imaging system, or other data storage or processing device, for example.

The interface 120 facilitates wireless communication and provides audio and video output, for example. The interface 120 may be a personal computer, a laptop computer, a tablet computer, a personal digital assistant, a handheld computer, a cellular phone, or other data processing device. The wireless communication device 110 is a wireless, voice-enabled communication device for transmitting spoken word commands, for example. The wireless communication device 110 may be a wireless headset, wireless microphone, wireless radio, or other wireless communication device, for example. An example of a wireless headset is a Bluetooth®, WiFi, or 802.11g wireless headset. Alternatively, the communication device 110 may be an infrared communication device or may be connected by a wire to the interface 120.

In an embodiment, the interface 120 and the wireless communication device 110 may be integrated into a single unit (for example, a display screen integrated into a headset). In another embodiment, the interface 120 and/or the wireless communication device 110 may be worn by a user or are attachable to the user.

Bluetooth®, for example, is a standard for voice and data transfer over a wireless medium. Bluetooth wireless technology enables a variety of devices to be connected without the use of cables and enhances connectivity and information exchange capabilities between devices on a wireless network. The Bluetooth protocol uses a 2.4 GHz frequency band for wireless communication between electronic devices. Data is transmitted between devices via a short-range wireless 2.4 GHz connection rather than a physical cable connecting the devices. Devices may be synchronized to communicate with each other using Bluetooth technology.

Bluetooth includes multiple levels of data transfer protocols and data transfer functionality. Bluetooth supports a variety of system-level profiles for data transfer, such as an audio/video remote control profile, a cordless telephony profile, an intercom profile, an audio/video distribution profile, a headset profile, a hands-free profile, a file transfer protocol, a file transfer profile, and/or an imaging profile. Hardware, such as the wireless communication device 110 and the interface 120, is used to support Bluetooth wireless transmission in a personal area network (PAN) or other network.

Voice and speech recognition capability may be integrated with Bluetooth or other wireless communication through software. For example, a computer with a wireless interface card running Bluetooth software and voice recognition software, such as Microsoft Windows XP® or a standalone voice recognition software, may facilitate verbal control of a system.

The wireless communication device 110 is connected to the interface 120 via a wireless connection, infrared connection, wire connection, or other such connection. Electronic commands are transmitted between the device 110 and the interface 120 to establish the connection. A password or other authentication, such as voice or other biometric authentication, may also be used to establish the connection between the device 110 and the interface 120. A connection is established between the interface 120 and the remote device 130 as well. Once a connection has been established between the wireless device 110 and the interface 120, commands may be passed between the device 110 and the interface 120 and relayed to another system, such as the remote system 130.

In an embodiment, the wireless communication device 110 is used to transmit commands and/or data to the remote system 130 via the interface 120. For example, an operator speaks, and the speech is received at the device 110. Alternatively, the communication device 110 may transmit directly to the remote system 130. Audio input from the wireless communication device 110 is transferred via asynchronous and/or synchronous layer communication. A Bluetooth headset profile, for example, may employ asynchronous (ACL) and synchronous (SCO) layers from a generic audio distribution transport protocol to communicate between the interface 120 and the wireless device 110. The ACL layer may be used to manage on/off, volume, and device pairing data, for example, for operation of the communication system 100. The ACL layer has a bandwidth of 1 Mbps, for example, to accommodate higher quality voice or audio data. The SCO layer transmits voice data at a rate of, for example, 64 Kbps. The interface 120 interacts with the wireless communication device 110 and the remote system 130 and transmits audio data between the remote system 130 and the wireless device 110. The wireless communication device 110, the interface 120, and the remote system 130 may communicate up to a range of approximately 10 meters, for example.

Figure 2:
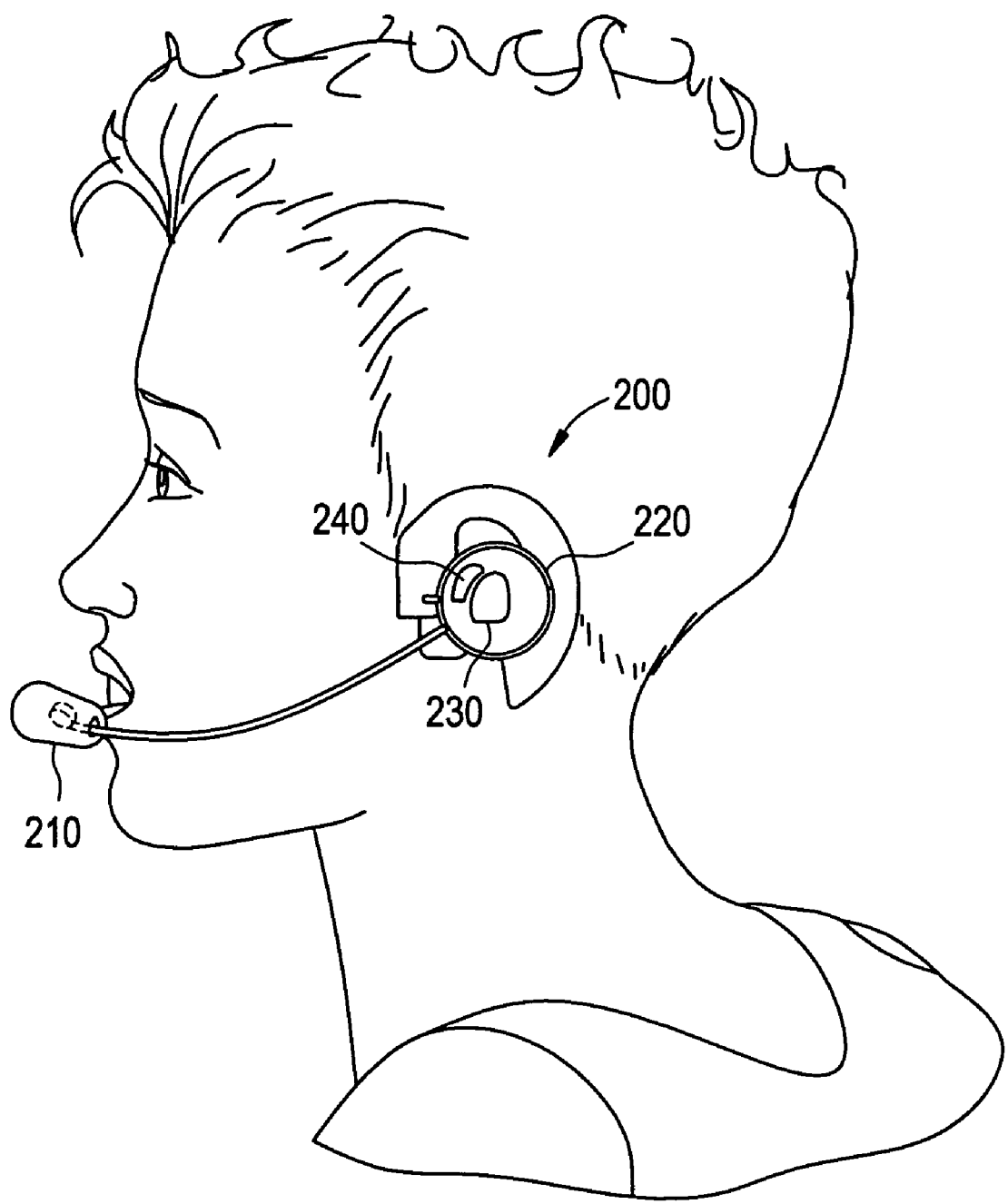
FIG. 2 illustrates an embodiment of a wireless headset used in accordance with an embodiment of the present invention.

The wireless communication device 110 may be implemented as a wireless headset. FIG. 2 illustrates an embodiment of a wireless headset 200 used in accordance with an embodiment of the present invention. The wireless headset 200 includes a microphone 210, an audio earpiece 220, speakers 230, and a wireless headset communication device 240. A person using the wireless headset 200 speaks into the microphone 210 and listens to audio sounds through the speakers 230 in the audio earpiece 220.

In operation, for example, a surgeon wears the wireless headset 200 within an operating room. The surgeon may request patient data, enter information about the current procedure, enter computer commands, and receive patient data using the wireless headset 200. To request patient data or enter computer commands, the surgeon speaks into the microphone 210. The request or command is transmitted from the wireless headset communication device 240 within the audio earpiece 220 of the wireless headset 200 to a local device via an interface device. The local device then executes command(s) received from the wireless headset communication device 240 within the wireless headset 200. If the surgeon requests patient information, the local device retrieves the information. The local device may then transmit the patient information to the wireless headset communication device 240 within the wireless headset 200 for playback through the speakers 230 in the audio earpiece 220 or the local device may transmit the patient information to another output device, such as the interface 120, for display or playback.

Before a medical procedure, for example, a surgeon may put on the wireless headset 200. The surgeon may then sterilize the surgeon's hands by scrubbing and putting on surgical gloves. After the medical procedure has begun, the surgeon may desire to view existing patient medical information stored in a storage device or enter new medical information obtained during the procedure. Rather than touch an unsterile computer keyboard or unsterile mouse, which would require re-sterilizing the surgeon's hands by re-scrubbing and re-gloving, the surgeon may use a more hygienic input devices such as the wireless headset 200, 110 and the interface 120.

By using the wireless headset 200, the surgeon's sterilized hands do not contact an unsterile surface such as the computer keyboard or computer mouse. The surgeon may speak requests and commands into the microphone 210 of the wireless headset 200. The wireless headset 200 then transmits the requests from the wireless headset communication device 240 to a local computer terminal. The local computer terminal processes the requests and commands from the wireless headset communication device 240 in the wireless headset 200.

Thus a user with the wireless communication device 110 may interact with a variety of electronic devices, such as the remote system 130, using the interface 120. As the user enters different rooms in a medical facility, the device 110 and/or the interface 120 synchronizes with one or more electronic devices or systems in a particular room. The user may then operate the device(s) using speech commands via the wireless communication device 110 and the interface 120. The user may also retrieve data from the device(s) using the device 110 and the interface 120.

In operation, a radiologist or other healthcare practitioner may wear and/or carry the device 10 and the interface 120 as he or she moves throughout a healthcare facility. Connections between the device 110, the interface 120 and other electronic systems in the facility may differ between different locations throughout the facility. For example, when a radiologist walks into an examination room, the wireless communication device 110 and the interface 120 establish a connection with a data collection device, such as a patient monitor, ECG machine, and/or an imaging system, for example. The wireless connection, for example, may be authenticated by a password, voice verification, electronic code or signature, or other biometric or security code.

For example, a radiologist wears a Bluetooth wireless headset and carries a tablet PC. The radiologist enters a radiology reading room to review or enter image data. A computer in the room recognizes the wireless headset and tablet PC. That is, data is exchanged between the tablet PC and the computer to allow the tablet PC and the computer to synchronize. The radiologist is then able to access the computer via the tablet PC using voice commands at the headset. The radiologist may view, modify, and print images and reports using voice commands via the headset and tablet PC. The wireless headset and tablet PC enable the radiologist to eliminate excess clutter in a radiology workspace by replacing use of a telephone, keyboard, mouse, etc. with the wireless headset and tablet PC. The wireless headset and tablet PC or other similar device may simplify interaction with a plurality of devices and simplify a radiologist's workflow through use of a single interface point.

Figure 3:
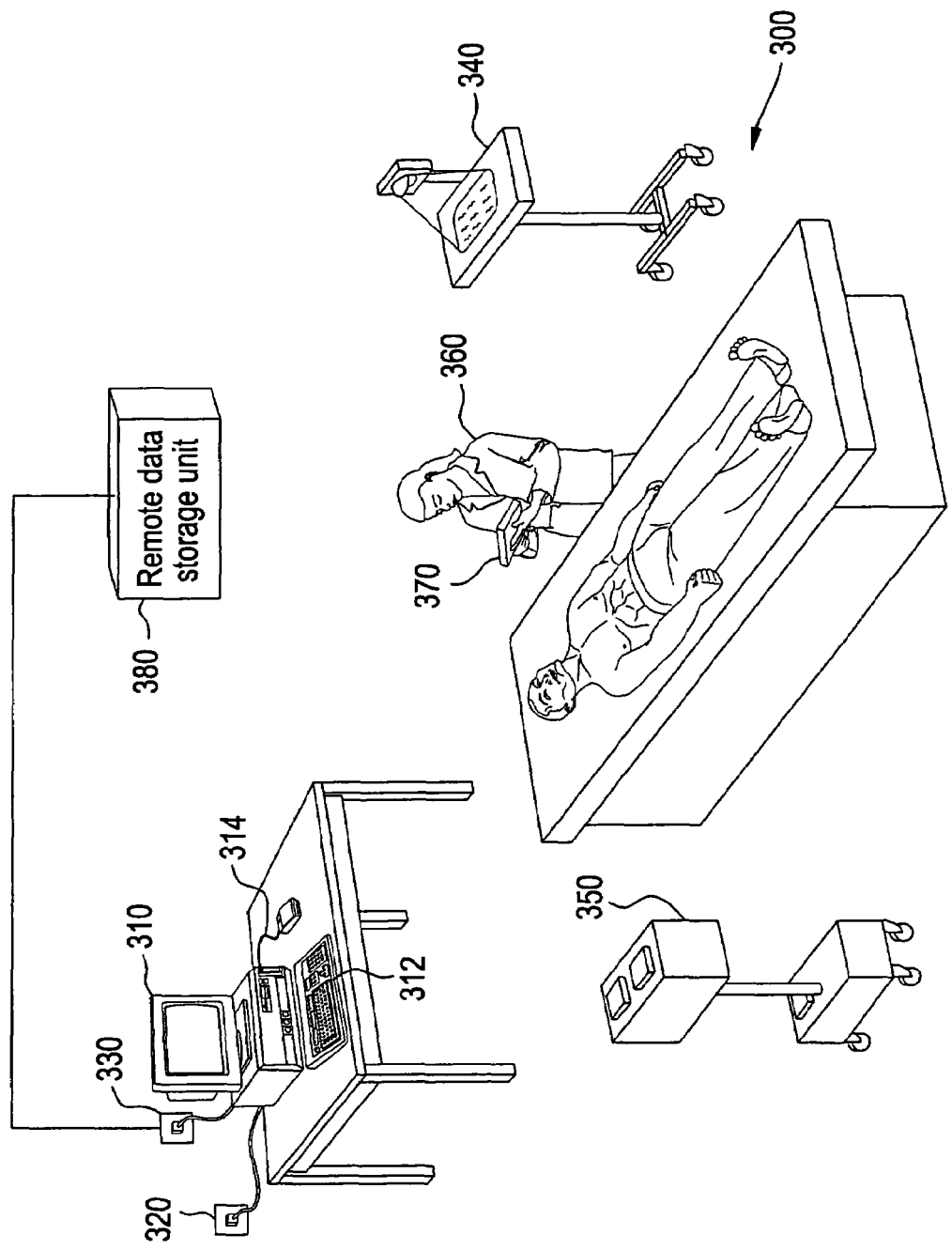
FIG. 3 depicts an example of a healthcare environment using wireless communication and control in accordance with an embodiment of the present invention.

FIG. 3 depicts an example of a healthcare environment 300 using wireless communication and control in accordance with an embodiment of the present invention. The environment 300 includes a local computer terminal 310, a hard-wired keyboard 312, a hard-wired mouse 314, a power outlet 320, a data port 330, a wireless input tray 340, a wireless interactive visual display system 350, a wireless headset 360, an interface device 370, and a remote data storage unit 380.

The remote data storage unit 380 stores patient medical information. The patient medical information may include medical data such as patient identifiers, images, lab results, medical diagnosis, and medical history. The remote data storage unit 380 transfers data to and from the local computer terminal 310 through the data port 330.

The local computer terminal 310 may be located within the environment 300, such as an operating room or in the vicinity of the operating room. The local computer terminal 310 is used by medical personnel to access the medical information stored in the remote data storage unit 380. The local computer terminal 310 plugs into and receives electrical power from the power outlet 320. The keyboard 312 and mouse 314 plug into local computer terminal 310. To access a patient's medical information and view medical data at the local computer terminal 310, medical personnel use their hands to manipulate the keyboard 312 and mouse 314 to control the local computer terminal 310. For example, information requests may be typed using the keyboard 312 or options may be selected on a screen by manipulating the mouse 314.

In addition to using the keyboard 312 or the mouse 314 to request patient medical information and enter new patient medical information, the wireless input tray 340, the wireless interactive visual display system 350, the wireless headset 360, and the interface 370 may be used. The wireless input tray 340, the wireless interactive visual display system 350, the wireless headset 360, and the interface 370 transfer data to and from the local computer terminal 310.

In operation, a surgeon may speak into the wireless headset 360 to request a patient's medical information. The wireless headset 360 transmits the surgeon's request to the local computer terminal 310. Communication between the wireless headset 360 and the local computer terminal 310 may use wireless communication standards such as the WiFi protocol or the Bluetooth standard. Communication between the wireless headset 360 and the local computer terminal 310 may be facilitated by the interface 370. The local computer terminal 310 processes the request and accesses the remote data storage unit 380 to retrieve the requested data. After the requested data has been retrieved by the local computer terminal 310 from the remote data storage unit 380, the local computer terminal 310 transmits the requested data to an output device within the operating room.

In the healthcare environment 300 of FIG. 3, the wireless headset 360, the interface 370, and the wireless interactive visual display system 350 may be used as output devices. If the requested data includes audio data, the audio data may be transmitted to either of the wireless headset 360, the interface 370, and/or the wireless interactive visual display system 350 for audio playback. If the requested data includes video data, the video data may be transmitted to the wireless interactive visual display system 350 and/or the interface 370 for display.

The surgeon may also speak into the wireless headset 360 to add data to a patient's medical record or issue commands to the local computer terminal 310. The wireless headset 360 transmits the data or commands to the local computer terminal 310. The local computer terminal 310 then executes commands received from the wireless headset 360 and transmits data to the remote data storage unit 380 for storage with the patient's other medical information.

In certain embodiments, voice commands may be used to navigate through clinical applications such as a picture archiving and communication system (PACS), a radiology information system (RIS), a hospital information system (HIS), and an electronic medical record (EMR). A user's speech may be used to execute commands in a system, transmit data to be recorded at the system, and/or retrieve data, such as patient reports or images, from the system.

Additionally, in certain clean rooms, such as surgical suites and catheterization labs in a hospital or clinic, use of a keyboard or mousing device, such as a mouse, a trackball, or a touchpad, may be impractical or unsanitary. Voice command and control provide a flexible and sanitary alternative in an environment where a doctor may be unable to manipulate a manual interface. Furthermore, voice command and control may be used to avoid or compensate for repetitive stress injuries due to manual access devices.

In certain embodiments, spoken words may be converted to text for storage and/or display at a remote system 130. Additionally, text at the remote system 130 may be converted to audio for playback to a user via the wireless communication device 110. For example, a radiologist or other healthcare practitioner may dictate reports without holding a microphone or other recording device. Using Bluetooth wireless technology, for example, dictation may be facilitated using voice recognition software on the interface 120 or the remote system 130. Alternatively, voice commands may be used to dial a telephony transcription service for remote dictation. Translation software allows dictation as well as playback of reports, lab data, examination notes, and image notes through the wireless communication device 110. Audio data may be review in real-time in stereo sound via the device 110. For example, a digital sound file of a patient heartbeat may be reviewed by a physician remotely through a Bluetooth headset.

The wireless communication device 110 and interface 120 may also be used to communicate with other medical personnel in a facility. For example, a user may page another practitioner for a consultation using the wireless communication system 100. Alternatively, the wireless communication system 100 may be used to telephone another practitioner. Thus, the user may be away from a phone and still communicate with others inside or outside the medical facility. In an embodiment, the wireless communication system 100 allows a healthcare practitioner to check voicemail messages or other communications remotely.

Certain embodiments may improve reporting by healthcare practitioners and allow immediate updating and revising of reports using voice commands. Clinicians may order follow-up studies at a patient's bedside or during rounds without having to locate a mouse or keyboard. Additionally, reports may be signed verbally, eliminating delay or inconvenience associated with a written signature.

The wireless communication system 100 may also be used with voice over Internet protocol (IP) to transmit voice audio data. For example, a specialist may call a referring doctor without picking up a phone. A radiologist may consult a colleague without paging the colleague. Additionally, voice over IP may be used to order additional images or tests.

Certain embodiments provide voice authentication to access clinical systems. The wireless communication device 110 working with the interface 120 may access the remote system 130 using voice commands. A user's voice print, a password, or a combination of voice and password authentication, for example, may be used to authenticate the user for access to the remote system 130. Verbal authentication may provide improved and more efficient system security over traditional typed password entry.

Figure 4:
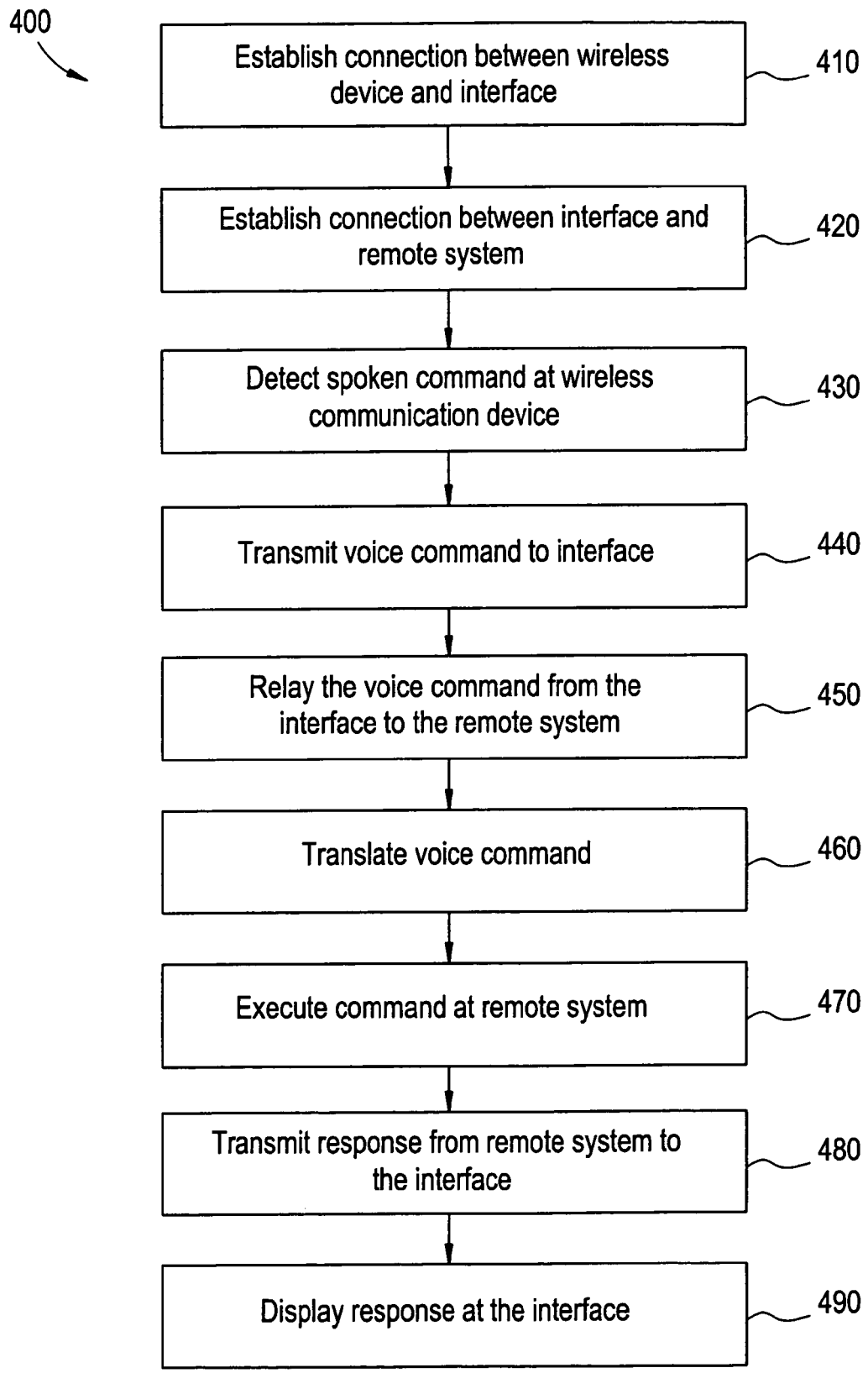
FIG. 4 shows a flow diagram for a method for wireless voice communication in a clinical workflow in accordance with an embodiment of the present invention.

FIG. 4 shows a flow diagram for a method 400 for wireless voice communication in a clinical workflow used in accordance with an embodiment of the present invention. First, at step 410, a connection is established between the wireless communication device 110 and the interface 120. Data packets are transmitted between the wireless device 110 and the interface 120 to establish a communication link between the device 110 and the interface 120. The communication link may also be authenticated using voice identification or a password, for example.

Then, at step 420, a connection is established between the interface 120 and the remote system 130. Data packets are transmitted between the interface 120 and the remote system 130 to establish a communication link between the interface 120 and the remote system 130. The communication link may also be authenticated using voice identification or a password, for example. After the communication links have been established, a user may communicate with the remote system 130 via the wireless communication device 110 and the interface 120.

Next, at step 430, a user speaks a command that is detected by the wireless communication device 110. At step 440, the voice command is transmitted to the interface 120. Then, at step 450, The interface 120 relays the voice command to the remote system 130. At step 460, the received voice command is translated by the remote system 130. Software running at the remote system 130 translates the spoken command to a command executable by the remote system 130.

Then, at step 470, the command is executed by the remote system 130. For example, a program may be executed at the remote system 130 in response to the voice command. Alternatively, for example, data may be retrieved at the remote system 130 in response to the voice command. A test or image acquisition, for example, may be initiated at the remote system 130 in response to the voice command. In another embodiment, a plurality of voice commands may be transmitted to the remote system 130 and executed.

Next, at step 480, a response is transmitted from the remote system 130 to the interface 120. For example, an acknowledgement of an action may be transmitted to the interface 120. Alternatively, for example, data retrieved at the remote system 130 may be transmitted to the interface 120. At step 490, the response may be displayed at the interface 120. A user may view the results at the interface 120. Alternatively, the interface 120 may relay the response to the wireless communication device 110 for audio broadcast to the user.

The wireless communication device 110 and the interface 120 may be used to communicate with a variety of remote systems and devices. For example, the device 110 and the interface 120 may control and retrieve data from an imaging system, a computer, an image or data storage system (such as a PACS), a telephone system, an electronic mail system, a surgical navigation system, and/or other electronic system in a healthcare facility. In an embodiment, the wireless communication device 110 may communicate directly with the remote system 130. Alternatively, the interface 120 may be integrated with the wireless communication device 110.

In an embodiment, gaze tracking may be used in place of or in addition to voice command for communication and transfer with a remote system. For example, a gaze tracking device may be used with the interface 120 to communicate with the remote system 130. By tracking where a user is focusing or fixating his or her visual attention, an accurate measure of user intent may be inferred. Eye or gaze tracking may be faster and more efficient than a mechanical pointing or selecting device.

The gaze tracking device may be based on a camera system (e.g., visible light or infrared), for example, and may be active or passive. For example, light may be reflected off of the user's pupil(s) and detected. Light may also be reflected off of the front and rear surfaces of the cornea(s) and lenses of the user's eye(s) and detected or recorded. Repeated measurements track a change in the user's gaze. Alternatively or in addition, a user's gaze may be tracked based on movement of the user's head via a camera or position sensor, for example. A position of the user's gaze and/or head in a reference coordinate system and/or with respect to a reference point, such as a location on a display, may be determined. In an embodiment, a plurality of measurements may be obtained to determine a user's line of sight and/or head angle, for example.

The gaze tracking device may include head gear, such as goggles or other ocular device, for a user to wear and/or may use a display-mounted camera or sensor, for example. In an embodiment, the gaze tracking device is calibrated for a user. By tracking a user's gaze, a system may initiate communication, selection, and/or function at a remote system, for example.

Figure 5:
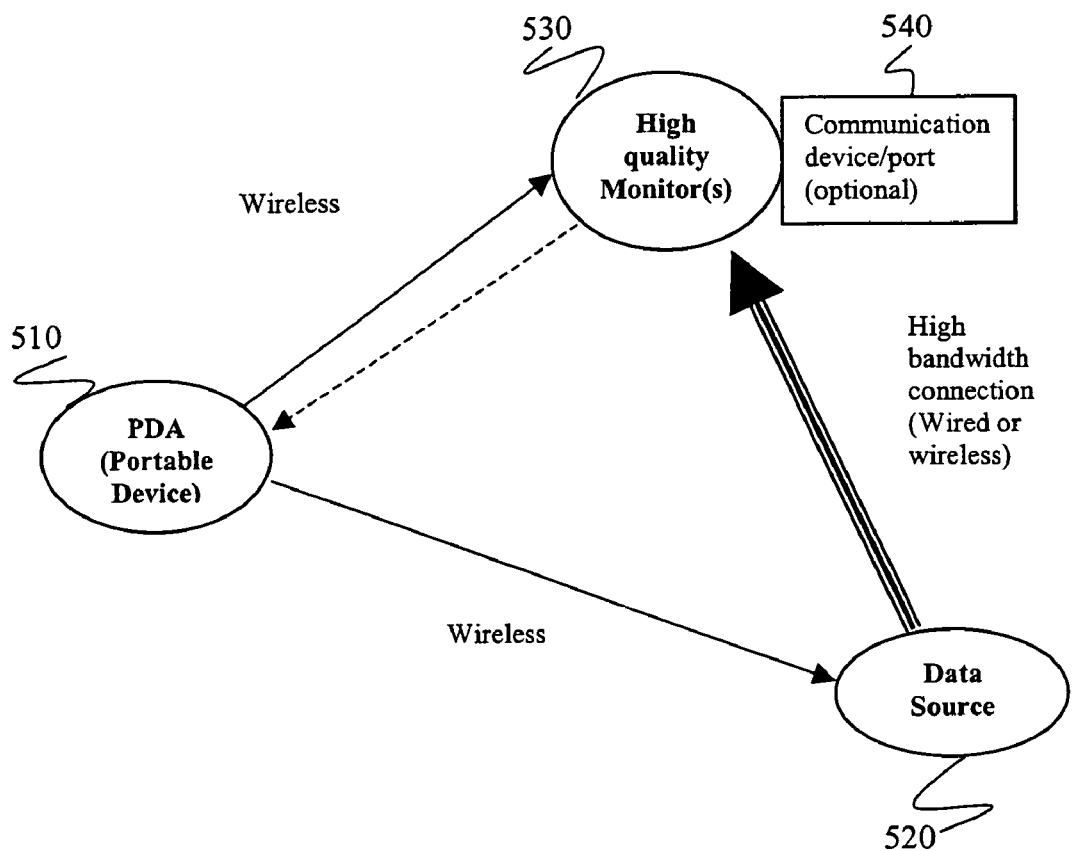
FIG. 5 illustrates a mobile display system used in accordance with an embodiment of the present invention.

Voice, gaze tracking, and/or other remote command technology may be applied to remotely display images and/or other data on a display. FIG. 5 illustrates a mobile display system 500 used in accordance with an embodiment of the present invention. The system 500 includes a portable device 510, a data source 520, and a display device 530. In an embodiment, the system 500 may include a plurality of display devices 530. The system 500 may also include a communication device 540 connected to the display device 530.

The portable device 510 is capable of wired and/or wireless communication with the data source 520 and display device 530. The data source 520 is capable of wired and/or wireless communication with the display device 530 and/or portable device 510. The display device 530 is capable of wired and/or wireless communication with the portable device 510. The communication device 540 is capable of wired and/or wireless communication with the display device 530 and may be capable of wired and/or wireless communication with the portable device 510 and/or the data source 520.

The portable device 510 may be a PDA, mobile phone, laptop, pocket personal computer, ultra personal computer, or other handheld or portable device, for example. In an embodiment, the portable device 510 may be similar to the interface 120 described above. The portable device 510 may be used to access and/or query patient information, images, and other data from a data source 520, such as a PACS, RIS, HIS, CIS, or other information system. The portable device 510 may be equipped to communicate with the data source 520 throughout a clinical environment, such as a hospital (via wireless communication, for example), or may use access points at certain locations in the clinical environment (via wireless and/or wired communication, for example).

The display device 530 is a display device displaying information from the data source 520 and/or the portable device 510. The display device 530 is associated with an identifier, such as an identification number, code or signal. The display device 530 may be a CRT, LCD, flat panel, projection, DLP or other display device, for example. The display device 530 may be a high quality and/or diagnostic quality display, for example. In an embodiment, the display device is a "dumb" display device that receives data from an external source and displays that data and has no direct user input. For example, the portable device 510 identifies the display device 530 using the associated identifier. The portable device 510 requests information from the data source 520 which is then displayed at the display device 530. Alternatively, the display device 530 may have a user and/or web-based interface for direct user interface (e.g., for users without a portable device 510).

The display device 530 may include a plurality of display devices. The display device 530 may be a stationary and/or mobile display device, for example. The display device 530 may be located anywhere in a clinical environment.

In an embodiment, the communication device 540 is attached and/or in wired or wireless communication with the display device 530. The communication device 540 may be integrated with the display device 530. The device 540 allows the display device 530 to be identified by the portable device 510 (e.g., automatically or by user authentication). The communication device 540 may communicate with the portable device 510 via wireless and/or wired communication, such as short-range infrared communication or transmission of the display device's serial number from the portable device to the communication device 540. In an embodiment, the display device 530 may be automatically identified based on a proximity of the portable device 510 to the display device 530 (e.g., radio frequency identification).

In an embodiment, the portable device 510 sends a display device 530 identification and a request for data to the data source 520. The data source 520, such as a PACS server, transmits or "pushes" the data, such as images and/or patient information, to the selected display device 530. In an embodiment, the wired and/or wireless connection between the data source 520 and the display device 530 is a high bandwidth connection allowing rapid transfer of data to the display device 530 for display. In an embodiment, a communication protocol between the portable device 510 and the data source 520 includes a conflict resolution scheme in case more than one portable device 510 is requesting data display on a single display device 530.

In operation, a user uses the portable device 510 (for example, a PDA) in a healthcare environment (for example, a hospital). The portable device 510 may be used for data entry as well as data retrieval, for example. The user may use the portable device 510 to retrieve and/or enter data from the data source 520. Data retrieved from the data source 520 may be displayed at the portable device 510 and/or the display device 530. A user may operate the portable device 510 directly via a user interface and/or via a wireless communication device, such as the wireless communication device 110 or wireless headset 200, described above.

The user requests image data from the data source 520 via the portable device 510. The data source 520 transmits the image data to the display device 530 for display. The user may then manipulate the display device 530 and/or the image data displayed via the display device 530. In an embodiment, a user may be authenticated prior to retrieval and/or display of image data. Thus, the user may view image data on a diagnostic-quality display.

Figure 6:
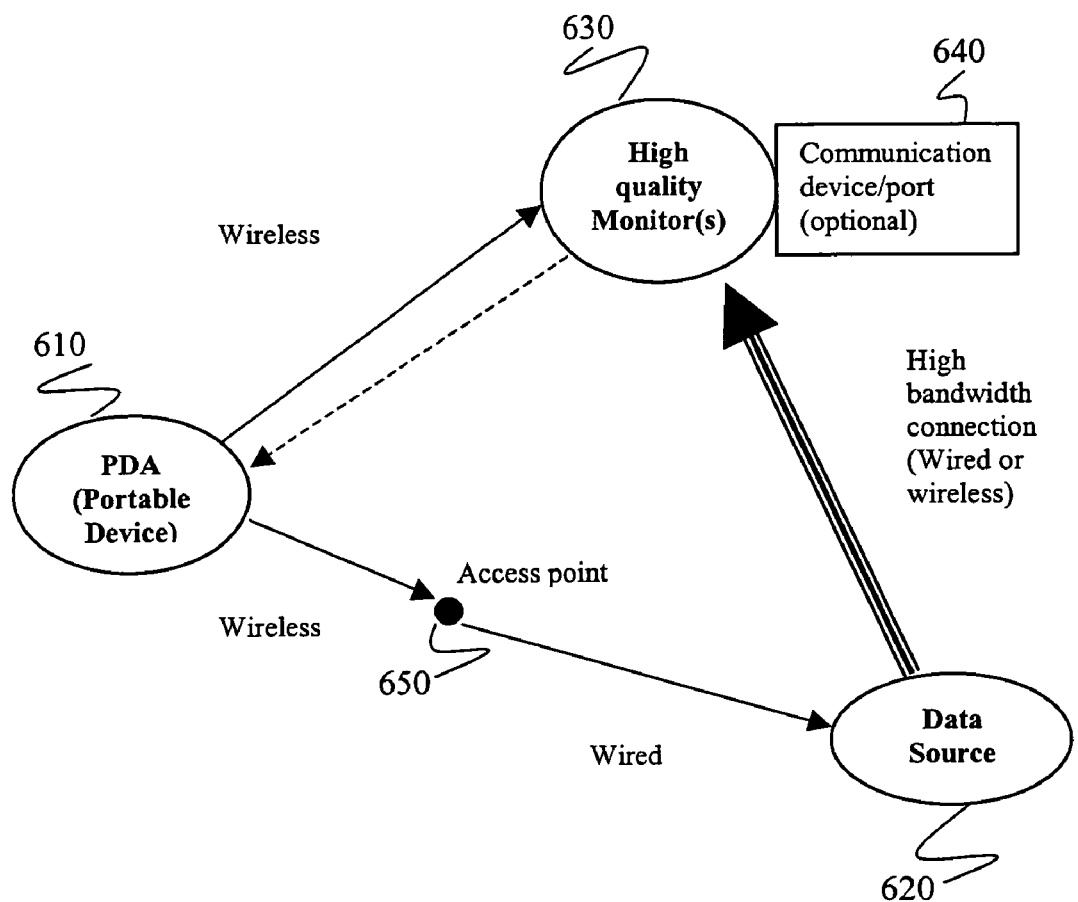
FIG. 6 illustrates a mobile display system used in accordance with an embodiment of the present invention.

FIG. 6 illustrates a mobile display system 600 used in accordance with an embodiment of the present invention. The system 600 includes a portable device 610, a data source 620, a display device 630, and an access point 650. In an embodiment, the system 600 may include a plurality of display devices 630. The system 600 may also include a communication device 640 connected to the display device 630. In an embodiment, the portable device 610, data source 620, display device 630, and/or communication device 640 may be similar to the portable device 510, data source 520, display device 530, and/or communication device 540 described above in relation to FIG. 5. The system 600 may function similarly to the system 500, as described above, for example.

The system 600 includes at least one access point 650 for relaying communications between the portable device 610 and the data source 620. The access point 650 may be a router, modem, hub, repeater, relay, and/or other wired/wireless access point, for example. The access point 650 connects the portable device 610, the data source 620, and/or other device in a healthcare environment to create a network. The access device 650 may arbitrate between a plurality of portable devices 610 or other devices seeking access to the data source 620. In an embodiment, the connection between the portable device 610 and the access device 650 is a wireless connection, and the connection between the access device 650 and the data source 620 is a wired connection, for example. The access device 650 relays data between the portable device 610 and the data source 620. The system 600 may include a plurality of access devices 650 to allow one or more portable devices 610 to connect to one or more data sources 620 to display data on one or more display devices 630 throughout a healthcare environment, for example.

Figure 7:
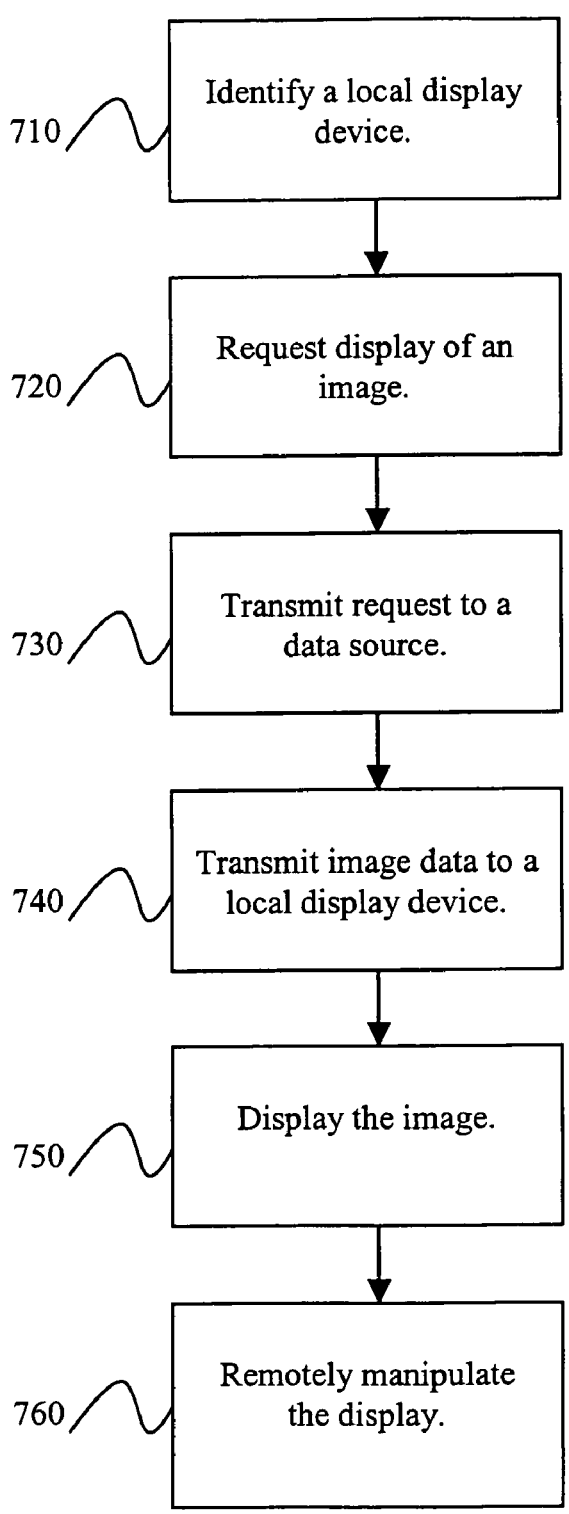
FIG. 7 illustrates a flow diagram for a method for remote display of high quality images used in accordance with an embodiment of the present invention.

FIG. 7 illustrates a flow diagram for a method 700 for remote display of high quality images used in accordance with an embodiment of the present invention. First, at step 710, a user identifies a local display device. For example, a surgeon selects a display in the operating room from a list on a Bluetooth-enabled personal digital assistant (PDA) and transmits a capture signal from the PDA to the display using wireless communication. Next, at step 720, a user requests display of an image. For example, a surgeon tries to retrieve an x-ray image of a patient's brain during surgery using a Bluetooth-enabled PDA and headset. Then, at step 730, the request for the image is transmitted to a data source. For example, the PDA transmits the image data request to a PACS workstation. The request may be transmitted to the workstation via a wireless connection, via a wired connection, relayed via an access point, etc.

Next, a step 740, the image data is transmitted to the identified local display. For example, the PACS system transmits the image data to a high-quality flat panel display in the operating room. Data may be transferred via a high bandwidth wired and/or wireless connection, for example. In an embodiment, image data is transferred directly from the data source to the display. The local display may be one of several displays in a healthcare environment identified by proximity and/or request from a portable device such as a PDA, for example. At step 750, the image is displayed for the user. For example, the surgeon views the brain image on the local display. Then, at step 760, the display may be remotely manipulated by the user. For example, the surgeon may use the PDA to zoom, resize, reposition, move, highlight, and/or otherwise manipulate the image displayed and/or display parameters. When the surgeon moves to a reading room to review images after surgery, the surgeon may request images from another data source and display the images at a display in the reading room to review images obtained during surgery, for example.

Thus, certain embodiments provide an improved or simplified workflow for a clinical environment, such as radiology. Certain embodiments allow a user to operate a single interface device with wireless communication to access functionality and transfer data in any given environment in a healthcare facility. Certain embodiments provide a system and method for a user to consolidate the workflow of all devices in an environment, such as a desktop or operating room, into one wireless, voice-enabled, digital workflow. Certain embodiments provide a system and method for a user to activate and perform wireless voice authentication. Certain embodiments provide a system and method for wireless voice data entry, such as wireless voice order entry and confirmation, wireless digital voice dictation, and wireless voice signature. Certain embodiments provide wireless voice control, such as wireless voice control of clinical application software, wireless clinical review of audio data, and wireless voice over IP conferencing. Certain embodiments provide wireless communication and control via other methods in addition to voice. For example, eye ball or gaze tracking, subvocal, and/or other method of control may be used similar to voice command described above.

Certain embodiments of the present invention provide increased efficient and throughput for medical personnel, such as radiologists and physicians. The system and method reduce desktop and operating room clutter, for example. Certain embodiments provide increased security for clinical applications and data through biometric authentication. Repetitive motion injuries may also be reduced or eliminated.

Certain embodiments provide a portability solution for images using a diagnostic quality display with minimal impact on user workflow. For example, a user may not have to sit at a stationary display device or directly upload images to a stationary display device, for example. Certain embodiments allow on-demand viewing of patient images anywhere a display device is available in a healthcare environment. Certain embodiments allow viewing of images and/or data from commonly-used modalities, such as radiography, that may not otherwise be viewed on non-diagnostic quality displays. By displaying images from a data source directly on a display device, extra storage space is minimized, as are time and inconvenience. A plurality of wired and/or wireless communication protocols may be used to communicate between the portable device, data source, and display device. Rather than being forced to interact with a stationary display device, user access/query may be accomplished via a portable device. Users may use their own portable device to access a variety of systems and display a variety of information without having to learn additional user interfaces, etc.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for remote image display to facilitate a clinical workflow in a clinical environment, said system comprising:
   a data source including clinical image data related to a patient, said data source transmitting said image data in response to a request;
   an identifiable display device displaying image data transferred from said data source, said identifiable display device being associated with an identifier to identify said display device among a plurality of display devices, said data source being external to said identifiable display device; and
   a portable device capable of retrieving said image data from said data source and displaying said image data on said portable device, said portable device identifying said display device using said identifier associated with said identifiable display device to select said display device from among the plurality of display devices across a plurality of locations in the clinical environment, said portable device requesting image data transfer from said data source to said display device wherein image data transferred to said display device from said data source is transferred without passing through said portable device to be relayed to said data source,
wherein said data source transmits said image data in response to a request specifying requested image data and target display device.

2. The system of claim 1, further comprising an access point for relaying communication between said portable device and said data source.

3. The system of claim 1, wherein said display device comprises a diagnostic quality display.

4. The system of claim 1, wherein said display device comprises a uniquely identifiable display device.

5. The system of claim 1, wherein said data source further includes non-image data.

6. The system of claim 5, wherein said display device is capable of displaying said non-image data.

7. The system of claim 1, wherein communication between said portable device and said data source comprises wireless communication.

8. The system of claim 1, wherein communication between said data source and said display comprises wireless communication.

9. The system of claim 1, wherein identification between said portable device and said display device occurs through wireless communication.

10. The system of claim 1, wherein said portable device comprises one of a personal digital assistant (PDA), mobile phone, laptop computer, pocket personal computer or ultra personal computer.

11. A method for remote display of images in a healthcare environment to facilitate a clinical workflow, said method comprising:
associating a display device with an identifier;
identifying the display device, with a portable device that is capable of retrieving and displaying image data from an external data source, using the identifier associated with the display device to identify said display device among a plurality of display devices in a plurality of locations in the healthcare environment;
requesting a transfer of image data from the external data source to said display device using said portable device wherein image data transferred to said display device from said data source is transferred without passing through said portable device to be relayed to said data source, wherein said data source transmits said image data in response to a request specifying requested image data and target display device; and
displaying said data at said display device.

12. The method of claim 11, wherein said requesting step further comprises requesting said transfer of said image data from said data source via a wireless connection.

13. The method of claim 11, wherein said display comprises a diagnostic quality display.

14. The method of claim 11, wherein said identification step occurs through wireless communication.

15. The method of claim 11, further comprising relaying said request for data via an access point to said data source.

16. The method of claim 11, further comprising controlling said display device.

* * * * *

UNITED STATES PATENT AND TRADEMARK OFFICE
CERTIFICATE OF CORRECTION

PATENT NO.       : 7,613,478 B2  
APPLICATION NO.  : 10/991570  
DATED            : November 3, 2009  
INVENTOR(S)      : Jabri et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1113 days.

Signed and Sealed this

Nineteenth Day of October, 2010

David J. Kappos  
*Director of the United States Patent and Trademark Office*